United States Patent [19]

Leszczynski

[11] Patent Number: 5,277,065
[45] Date of Patent: Jan. 11, 1994

[54] DETECTOR WITH RINGDOWN FREQUENCY MATCHING

[75] Inventor: Nicholas Leszczynski, Amherst, N.Y.

[73] Assignee: Magnetrol International, Inc., Downers Grove, Ill.

[21] Appl. No.: 7,845

[22] Filed: Jan. 22, 1993

Related U.S. Application Data

[62] Division of Ser. No. 578,558, Sep. 4, 1990.

[51] Int. Cl.[5] .............................................. G01N 29/00
[52] U.S. Cl. ......................................... 73/597; 367/903
[58] Field of Search ............... 73/597, 602, 632, 290 V; 310/317, 318; 367/903, 908

[56] References Cited

U.S. PATENT DOCUMENTS

| | | | |
|---|---|---|---|
| 3,745,520 | 7/1973 | Barrett | 340/3 D |
| 3,985,030 | 10/1976 | Charlton | 73/290 V |
| 4,000,650 | 1/1977 | Snyder | 73/290 V |
| 4,114,441 | 9/1978 | Magri | 73/290 V |
| 4,169,255 | 9/1978 | Hulsman et al. | 367/100 |
| 4,221,004 | 9/1980 | Combs et al. | 367/114 |
| 4,299,114 | 11/1981 | Silvermetz et al. | 73/1 H |
| 4,320,659 | 3/1982 | Lynnworth et al. | 73/589 |
| 4,687,962 | 8/1987 | Elbert | 310/317 |
| 4,793,178 | 12/1988 | Ahern et al. | 73/151 |
| 4,901,245 | 2/1990 | Olson et al. | 73/290 V |
| 4,914,951 | 4/1990 | Koelpin et al. | 73/597 |
| 5,157,639 | 10/1992 | Leszczynski | 367/908 |

OTHER PUBLICATIONS

Product brochure entitled "Sensall System 8100 Ultrasonic Continuous Liquid Level Transmitter".
Document entitled "System 8100—Technical Description".

*Primary Examiner*—Louis Arana
*Attorney, Agent, or Firm*—Marshall, O'Toole, Gerstein, Murray & Borun

[57] ABSTRACT

An ultrasonic detector of the type for determining the level of a liquid within a tank or the magnitude of the flow of liquid within a conduit. The detector includes a transducer that generates bursts of ultrasonic energy and receives echoes of the energy bursts. The frequency at which she transducer transmits energy bursts is automatically adjusted to substantially match the ringdown frequency of the transducer. The detector distinguishes between true echo signals and spurious echo signals by determining whether the frequency of the echo signals generated by the transducer substantially matches the frequency at which the corresponding energy bursts were transmitted.

20 Claims, 8 Drawing Sheets

DETECTOR WITH RINGDOWN FREQUENCY MATCHING

BACKGROUND OF THE INVENTION

This application is a division of U.S. Ser. No. 578,558, filed Sep. 4, 1990.

The present invention relates to ultrasonic level or flow detectors that have the capability of automatically adjusting the frequency at which ultrasonic energy is transmitted.

Ultrasonic detectors may be used to determine the level of a liquid in a tank or the magnitude of the flow of liquid within a conduit. Such detectors have transducers that emit bursts of ultrasonic energy and respond to echoes of the bursts that are reflected by various surfaces. For example, a detector that determines the level of a liquid in a tank transmits energy bursts towards the liquid surface and detects when echoes of the energy bursts are received. The detector then determines the liquid level based upon the time difference between the transmission of an energy burst and the receipt of the corresponding echo. This travel time of an energy burst is directly related to the distance from the transducer to the liquid surface.

Ultrasonic detectors typically have piezoceramic transducers that convert trains of electrical pulses into ultrasonic energy bursts. The transducers also convert the echoes they receive back into electrical signals. The efficiency of an ultrasonic transducer at converting the electrical pulse trains to energy bursts varies with the frequency at which the transducer is excited. It is known that such transducers optimally convert electrical signals to ultrasonic energy at their natural frequency of oscillation, which is referred to as their "ringdown" frequency. Any substantial departure from exciting a transducer with an electrical pulse train having a frequency that matches the ringdown frequency of the transducer may adversely affect the operation of the detector.

A conventional ultrasonic detector typically includes a pulse generator that generates the electrical pulse trains which excite the transducer. The frequency at which the pulse generator oscillates may be manually adjusted, for example with a potentiometer. Once the frequency is manually adjusted, the pulse generator generates pulse trains whose frequency is fixed.

After manufacture of an ultrasonic detector, the frequency of the pulse generator is manually adjusted by an operator so that it substantially matches the ringdown frequency of the transducer. This frequency adjustment is necessary since the ringdown frequency of one transducer may vary by about 5–10% from the ringdown frequency of another transducer.

This manual adjustment of the transducer excitation frequency has a number of disadvantages. One disadvantage is the time required to perform the frequency adjustment. Another disadvantage is that the ringdown frequency may drift with temperature and the age of the transducer. Thus, although the transducer excitation frequency is initially set correctly, it will not be set correctly when the temperature changes significantly and when the transducer ages. A third disadvantage is that the detector must be retuned when the transducer is replaced with a new transducer.

SUMMARY OF THE INVENTION

The present invention is directed to an ultrasonic detector of the type that may be used to determine the level of a liquid within a tank or the magnitude of liquid flow within a conduit and which has a frequency matching capability that automatically adjusts the frequency at which the transducer generates bursts of energy based upon the transducer ringdown frequency. The ringdown frequency is that frequency at which the conversion of electrical signals to ultrasonic energy is most efficient. Preferably, the transducer frequency is adjusted so that it substantially matches the ringdown frequency. The use of the ringdown frequency for transmission also results in increased sensitivity in detecting echo signals.

In accordance with the invention, a detector is provided with a transducer, means coupled to the transducer for detecting the ringdown frequency of the transducer, and means coupled to the transducer for automatically adjusting the frequency at which the transducer generates energy bursts to substantially match the transducer ringdown frequency. The transmission frequency may be considered to "substantially match" the ringdown frequency when those two frequencies differ by no more than about one percent. As a result, the frequency at which the transducer generates energy bursts will be optimally tuned, regardless of environmental conditions such as temperature variations and other conditions, such as the age of the transducer.

The ringdown frequency may be detected by generating an average ringdown frequency. The average ringdown frequency may be determined by transmitting multiple energy bursts from the transducer, and measuring the ringdown frequency corresponding to each burst. The ringdown frequency corresponding to each burst may be measured with the use of a "frequency gate," which defines a period of time during which the frequency is measured. The frequency gate may be shifted after the transmission of each energy burst.

These and other features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIG. 2b is a diagram of two waveforms generated in the zero-crossing detector circuit of FIG. 2a;

DETAILED DESCRIPTION OF A PREFERRED EMBODIMENT

Figure 1:
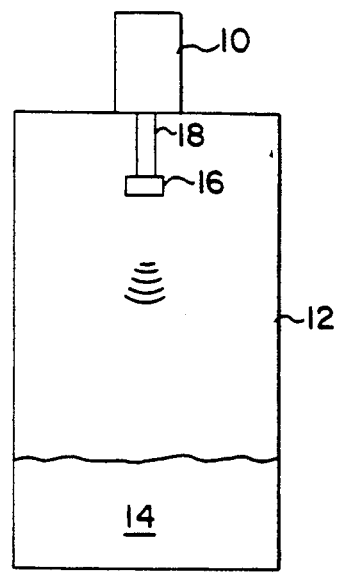
FIG. 1 is a schematic view of an ultrasonic detector in accordance with the invention shown attached to a container.

Referring to FIG. 1, a detector 10 in accordance with the invention is shown fixed to a container 12, such as a tank, containing a liquid 14. The detector 10 includes an ultrasonic transducer 16 connected via a shaft 18. The transducer 16, when triggered, periodically emits bursts of ultrasonic energy which are transmitted towards the liquid 14 and reflected back to the transducer 16 after reflection from the liquid surface. The reflected ultrasonic energy, or echoes, are converted by the transducer 16 to electrical signals. From these signals, the detector 10 determines the level of the liquid surface based upon the time between the transmission of the ultrasonic energy and receipt of the echoes.

While the detector 10 is shown in FIG. 1 to detect the liquid level, it could also be used to detect liquid flow. Detecting flow could be accomplished by detecting the height of liquid at the gauging point of a flume or weir, which is a well-known, conventional manner of detecting flow. The detector 10 can also detect the presence of objects or substances other than liquids, such as grain for example.

Figure 2:
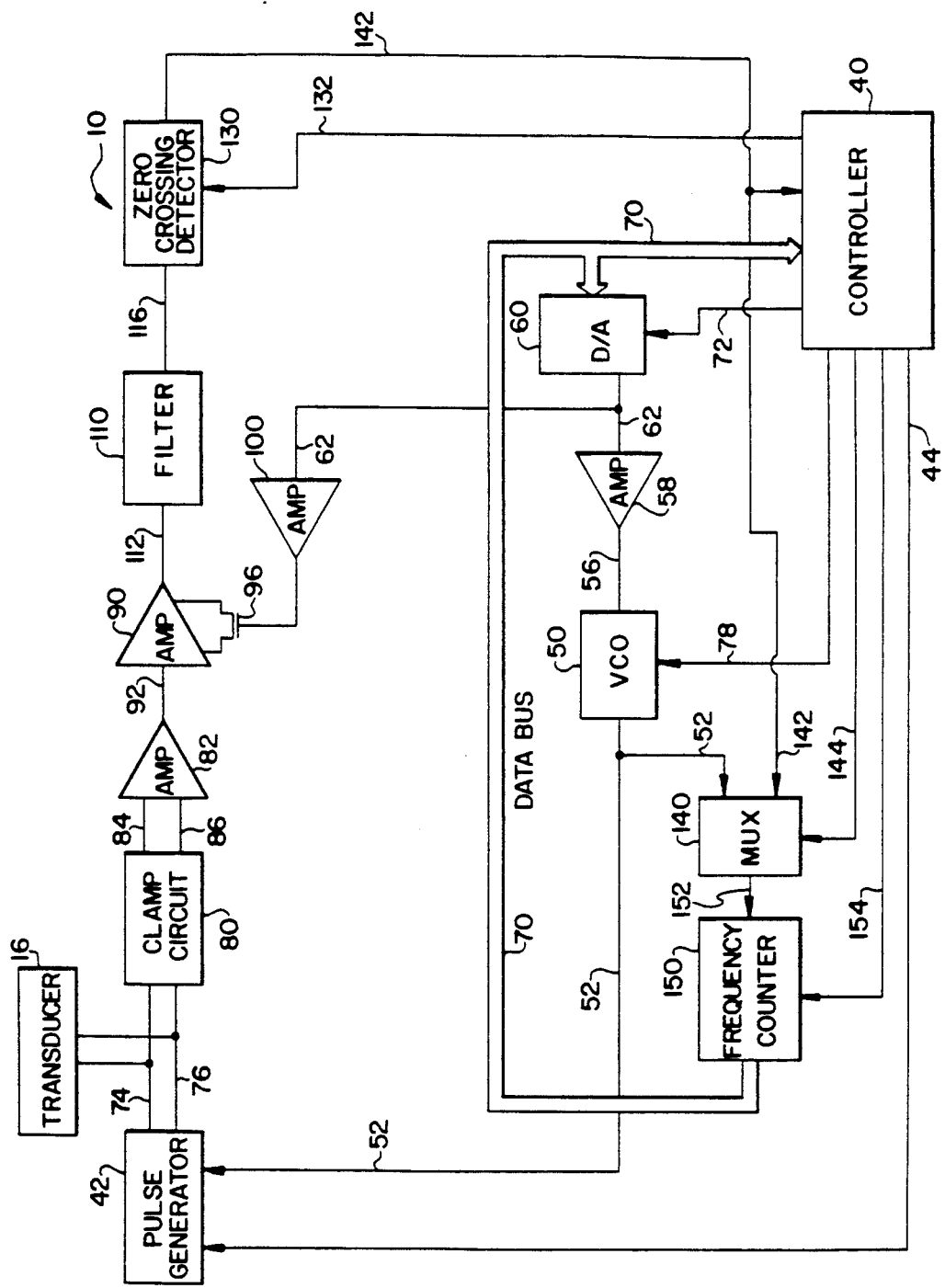
FIG. 2 is a block diagram of the electronics of the detector of FIG. 1.

A block diagram of the electronics of the detector 10 is shown in FIG. 2. The overall operation of the detector 10 is controlled by a controller 40, which may include any conventional microprocessor, data memory, software program memory, and associated interface circuits. The controller 40 has a programmable read-only memory (PROM) (not shown) in which a computer program is stored. The computer program, which is described in detail below, controls the operation of the detector 10.

The transducer 16 is periodically excited with electrical pulse trains transmitted from a pulse generator 42. The electrical pulses in the trains can have either a relatively high magnitude or a relatively low magnitude, as determined by a logic signal provided to the pulse generator 42 from the controller 40 via a line 44.

The frequency of each pulse train is controlled by a voltage-controlled oscillator (VCO) 50, which is connected to the pulse generator 42 via a line 52. This frequency may be generally in the range of 40 kHz to 50 kHz. The frequency at which the VCO 50 oscillates, and thus the frequency of the electrical pulse train, is determined by an analog voltage provided to the VCO 50 via a line 56. The analog voltage is generated by an amplifier 58 that is connected to a digital-to-analog (D/A) converter 60 via a line 62. The D/A converter 60 is connected to the controller 40 via a data bus 70 and has an enable line 72. The controller 40 controls the frequency at which the VCO 50 oscillates by sending an appropriate multi-bit digital signal to the D/A converter 60, which converts the digital signal to a corresponding analog voltage. After amplification, the analog voltage is supplied to the VCO 50 via the line 56. This analog voltage is a relatively low-level signal, which may vary between seven and nine volts, for example.

The duration of each pulse train generated by the VCO 50 is controlled by a logic signal, or "transmit gate," generated by the controller 40 and provided to the VCO 50 via a line 78.

Upon receiving a pulse train from the VCO 50, the pulse generator 42 transmits to the transducer 16 either a relatively high- or relatively low-amplitude pulse train via a pair of lines 74, 76. The pulses transmitted to the transducer 16 are on the order of several hundred volts. In response to receiving a pulse train on the lines 74, 76, the transducer 16 generates a corresponding burst of ultrasonic energy and transmits the burst to the interior of the tank 12. Any echoes of the energy burst that are received by the transducer 16 are converted by the transducer 16 back into electrical signals and provided on the lines 74, 76.

The lines 74, 76 are provided to a signal processing circuit that includes a clamp circuit 80, a fixed-gain amplifier 82 coupled to the clamp circuit 80 via a pair of lines 84, 86, and a variable gain amplifier 90 connected to the amplifier 82 via a line 92. The clamp circuit 80 reduces the magnitude of any electrical signals provided to the amplifier 82 via the lines 84, 86 to about 0.5 volt. The main purpose of the clamp circuit 80 is to prevent the high-voltage pulses generated by the pulse generator 42 from damaging the amplifiers 82, 90. The clamp circuit 80 does not substantially affect the electrical signals generated by the transducer 16, which correspond to echoes, since those electrical signals are typically smaller than 0.5 volt.

The variable-gain amplifier 90 controls the magnitude of the electrical signals received from the transducer 16. The gain of the amplifier 90 is determined by a control voltage provided to the gate of a field-effect transistor (FET) 96 connected to the amplifier 90. The control voltage, which acts to vary the resistance across the source and drain terminals of the FET 96, is generated by an amplifier 100 connected to the D/A converter 60 via the line 62. The controller 40 controls the gain of the amplifier 90 by providing the D/A converter 60 with a multi-bit digital signal. The digital signal is converted by the D/A converter 60 to an analog voltage, which is provided to the amplifier 100 that generates the gain control voltage. The single D/A converter 60 may be used to control both the VCO 50 frequency and the amplifier 90 gain since those values are never set simultaneously.

The electrical signal amplified by the amplifier 90 is provided to a bandpass filter 110 via a line 112. The bandpass filter 110 may comprise an active filter, such as a high-pass amplifier filter coupled to a low-pass amplifier filter.

The electrical signal output from the filter 110 via the line 116 is provided to a zero-crossing detector 130. The zero-crossing detector 130 performs several functions. One of these functions is to generate a zero-crossing signal indicative of the frequency of the ringdown signal generated on the line 116 immediately following the transmission of the energy burst. A second function is to generate a zero-crossing signal indicative of the frequency of the echo signal provided on the line 116. The third function is to generate an echo-detect signal when the magnitude of the echo signal surpasses a threshold voltage.

Figure 2A:
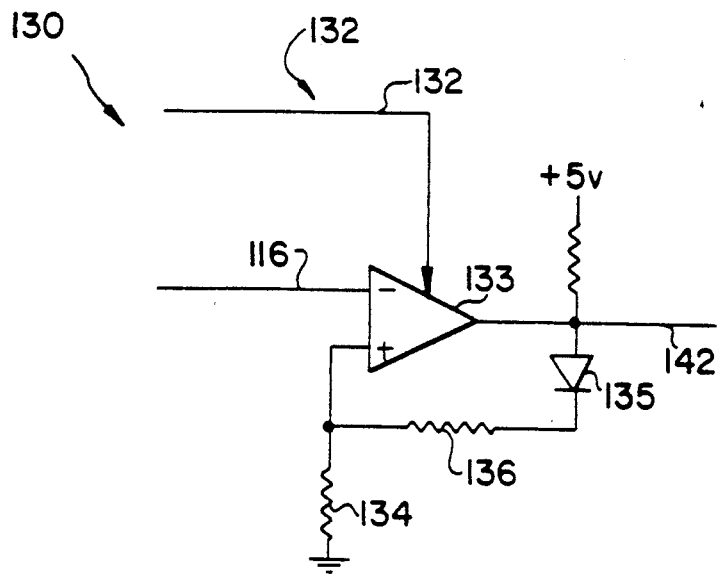
FIG. 2a is a circuit diagram of the zero-crossing detector schematically shown in FIG. 2.

A circuit diagram of one embodiment of the zero-crossing detector 130 is shown in FIG. 2a. The detector 130 comprises a comparator 133 having its inverting input connected to the line 116, its noninverting input connected to ground through a resistor 134, and its output connected to the line 142. A diode 135 and a resistor 136 are connected in series across the output and the noninverting input of the comparator 133 to provide hysteresis. When the output of the comparator is high, or about five volts, the voltage at the noninverting input of the comparator is 300 millivolts (mv). When the comparator output is low, or zero volts, the voltage at the noninverting input is zero volts.

Figure 2B:
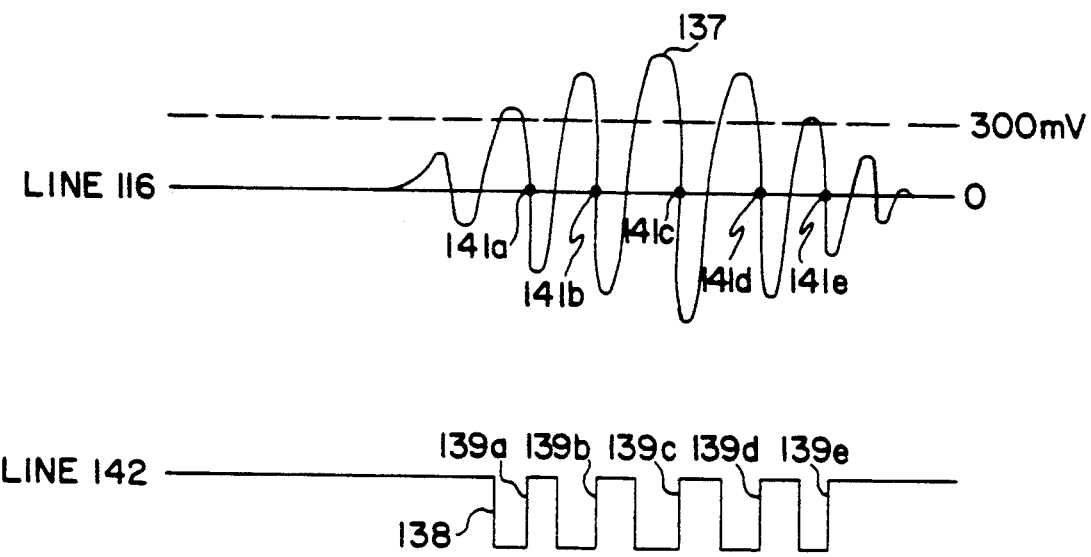

In operation, when the comparator 133 output is high, its output switches to low when the magnitude of the signal provided at its inverting input rises about 300 mv. When the comparator output is low, its output switches to high when the magnitude of the electrical signal provided to its inverting input falls below zero volts. This switching action is illustrated in FIG. 2b, in which an electrical echo signal 137 on the line 116 is shown with respect to the comparator 133 output on a line 142.

As can be seen, the first falling edge 138 of the signal on the line 142 is generated when the magnitude of the echo signal 137 first surpasses the 300 mv threshold. This falling edge is provided to the controller 40 via the line 142 as an echo-detect signal to signal the controller 40 that an echo signal having a sufficient magnitude has been received. This indicates the time of receipt of the echo.

The comparator output signal on the line 142 generates rising edges 139a–139e in response to the echo signal 137 falling below zero as indicated by points 141a–141e. The time difference between adjacent zero-crossing edges 139a–139e is used to determine the frequency of the echo signal 137 as described in more detail below. As described in more detail below, if the frequency of a received echo signal does not substantially match the frequency at which the ultrasonic energy burst was transmitted, the corresponding echo is rejected as being a spurious echo.

The specific manner in which the time of arrival of the echo is determined is not considered important to the present invention. Any type of detection circuit could be used in the practice of the invention to determine the time of arrival. For example, instead of determining when the magnitude of the echo signal surpasses a predetermined threshold, the detection circuit could comprise a peak detector that determines when the peak of the echo signal is received. The peak could be detected by sampling the echo signal at the output of the filter 110 at a high rate when the echo signal is expected, converting the samples to digital form via an A/D converter, and selecting the digital sample having the largest magnitude as the peak of the echo.

The zero-crossing detector 130 is activated by a logic signal, or "frequency gate," provided by the controller 40 via a line 132. The frequency gate is opened for a portion of the duration of the received echo signal or ringdown signal sufficient to obtain at least one pair of zero-crossings in order to determine the time period between two successive zero-crossings.

Referring back to FIG. 2, the output of the zero-crossing detector 130 is provided to a multiplexer 140 via the line 142. When the frequency of either the ringdown signal or the received echo signal is to be determined, the controller 40 provides a select signal to the multiplexer 140 via a line 144 to cause the multiplexer 140 to pass the output of the zero-crossing detector 130 to a frequency counter 150 via a line 152. The frequency counter 150 generates a binary count corresponding to the time duration between two adjacent zero-crossings. The actual time, and thus the frequency, is determined by the controller 40 from the binary count provided by the frequency counter 150. The binary count is transmitted from the counter 150 to the controller 40 via the data bus 70 when triggered by a logic signal provided to the frequency counter 150 by the controller 40 via a line 154.

The output of the VCO 50 is provided to the frequency counter 150 via the line 52 at certain time periods to measure the frequency of the pulse train generated by the VCO 50. As described in more detail below, the VCO output is periodically supplied to the frequency counter 150 so that the VCO frequency can be adjusted to match the ringdown frequency of the transducer 16.

OPERATION

The operation of the ultrasonic detector 10 is controlled by a computer program stored in the controller 40. The computer program comprises a main operating routine, a frequency match routine, and a sonar routine, which are described in detail below. These routines may be implemented as subroutines, interrupt service routines, or any other type of routine or program. The precise form of the routines is not considered important in the practice of the invention.

Main Operating Routine

Figure 3:
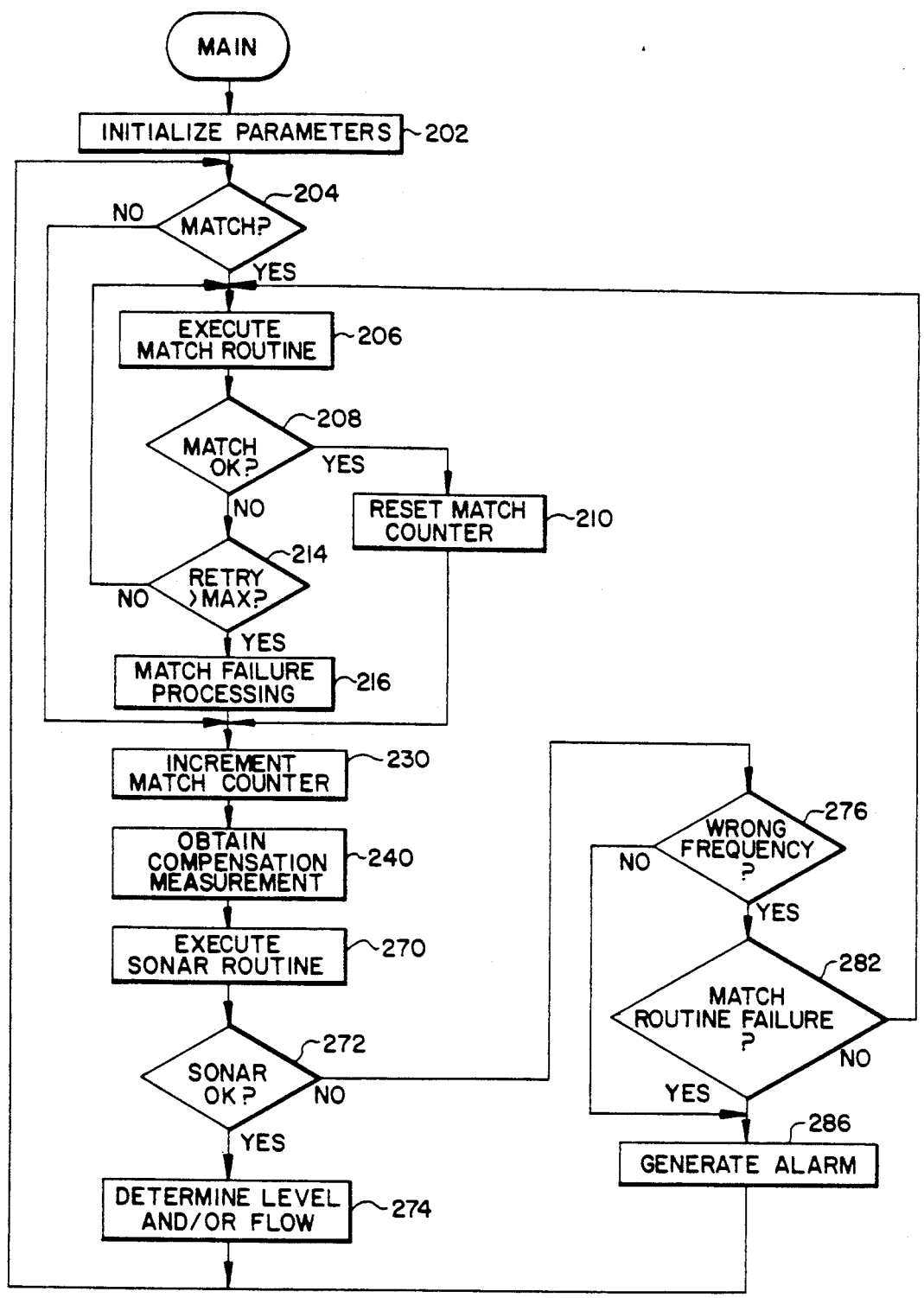
FIG. 3 is a flowchart of the main operating routine of the computer program stored in the controller schematically shown in FIG. 2.

A flowchart of the main operating routine is shown in FIG. 3. The main operating routine controls the overall operation of the detector 10 and determines when the frequency match and sonar routines are executed.

Now referring to FIG. 3, the main operating routine begins at step 202 where various parameters are initialized. One of these parameters is a match counter associated with the frequency match routine. The match counter determines how often the frequency match routine is executed by the main operating routine. For example, the frequency match routine may be executed once every 50 times the main operating routine cycles through its main loop.

Each time the main operating routine cycles through its main loop, it increments the match counter. When the match counter reaches its maximum count, the frequency match routine is performed. Upon completion of the match routine, the match counter is reset to zero. Thus, for example, if the maximum count of the match counter is 50, the frequency match routine will be performed once every 50 cycles of the main operating routine.

During the initialize parameters step 202, the match counter is set to its maximum value to force the frequency match routine to be performed during the first execution of the main loop of the main operating routine.

At step 204, the match counter is read to determine if it is time for the match routine to be executed. If it is, the match routine is performed at step 206. As described in detail below, the match routine causes the frequency at which the ultrasonic energy burst is transmitted to substantially match the ringdown frequency of the transducer 16. At step 208, if the match routine is successfully performed, the program branches to step 210 where the match counter is reset to zero. The program then branches to step 230.

If the match routine was not successfully executed as determined at step 208, the program branches to step 214, where the program determines whether the match routine has been performed unsuccessfully a maximum number of times. If not, the program branches back to step 206 where the match routine is again performed.

If the frequency match routine was attempted more than the maximum number of times as determined at step 214, the program branches to step 216 where match failure processing is performed. This processing includes setting the match counter to one less than its maximum count to force reexecution of the match routine during the next loop of the main operating routine. In addition, the digital signal sent to the 0/A converter 60 to control the VCO frequency, which is referred to herein as the "frequency vector," is set to its default value, which corresponds to an intermediate frequency. The program then branches to step 230.

At step 230, the match counter is incremented by one, and then the program branches to step 240, where a compensation measurement is obtained. The detector 10 may utilize either temperature compensation or reference-target compensation to account for variations in speed of the ultrasonic energy resulting from atmospheric conditions within the tank 12.

If temperature compensation is used, at step 240 the program would obtain the current temperature measurement from a temperature sensor (not shown). If reference-target compensation is used, at step 240 the program would transmit an energy burst and determine the flight time of the burst to a reference reflector (not shown). If desired, step 240 may only be executed once every 20 cycles of the main operating routine with the use of a counter like the match counter.

At step 270, the sonar routine is executed. Unlike the frequency match routine, the sonar routine is performed during each loop of the main operating routine. The sonar routine transmits a predetermined number of energy bursts to generate the average round-trip travel time of the bursts between the transducer 16 and the liquid surface. The level of the liquid surface is then determined based upon this average round-trip travel time.

If the execution of the sonar routine was successful as determined at step 272, the program branches to step 274 where the liquid level and/or flow is determined based upon the average round-trip travel time. The program then branches back to step 204 for the next execution of the main loop of the main operating routine. If the execution of the sonar routine was not successful as determined at step 272, the program branches to step 276.

As described below, the sonar routine checks the frequency of each received echo signal to make sure it is substantially the same as the frequency at which the corresponding energy burst was transmitted. If the frequency of any echo signal does not match, then that echo signal is not considered to correspond to the liquid level, but is considered to be a spurious echo signal that was generated by, for example, electrical noise due to the startup of a pump located adjacent the tank 12. If none of the echoes corresponding to the energy bursts transmitted during the sonar routine has the correct frequency, then a "wrong frequency" flag is set to one.

At step 276, the program determines whether the "wrong frequency" flag was set during the most recent execution of the sonar routine at step 270. If the "wrong frequency" flag was set, the program branches to step 282, where the program determines whether there was a previous failure of the match routine. If there was no match routine failure, the program branches back to step 206 where the match routine is again performed. If there was a match routine failure, the program branches to step 286, where an alarm is generated. The program then branches back to step 204.

Frequency Match Routine

The purpose of the frequency match routine is to match the frequency at which energy bursts are transmitted to the ringdown frequency of the transducer 16. This is done because a transducer is more efficient at converting electrical pulses to ultrasonic energy and vice versa at its ringdown frequency. The frequency at which the transducer 16 transmits energy bursts is controlled by, and is the same as, the excitation frequency of the transducer 16, which is the same frequency at which the VCO 50 generates pulses.

During the first portion of the frequency match routine, 40 energy bursts are transmitted and the frequency of the 40 corresponding ringdown signals is determined. The 40 frequency samples are then averaged to get an average ringdown frequency. The frequency at which the energy bursts are transmitted, which is controlled by the VCO 50, is then adjusted so that it is substantially the same as the average ringdown frequency. The burst transmission frequency is considered to substantially match the ringdown frequency when those two frequencies differ by no more than about one percent. Thus, for example, a transmission frequency of 49.5 kHz substantially matches a ringdown frequency of 50 kHz.

Figure 4A:
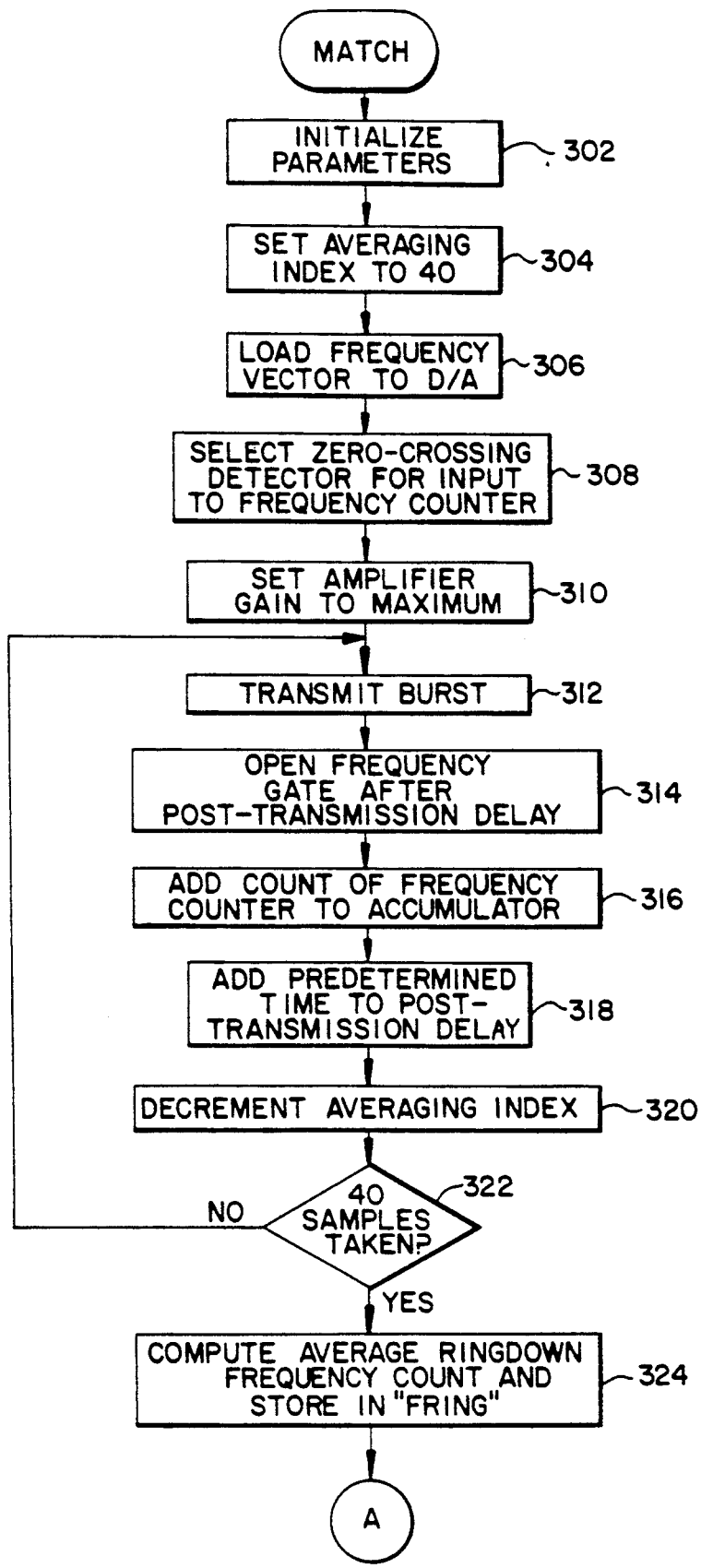
FIGS. 4a and 4b are a flowchart of a frequency match routine schematically shown in the main operating routine of FIG. 3.
Figure 4B:
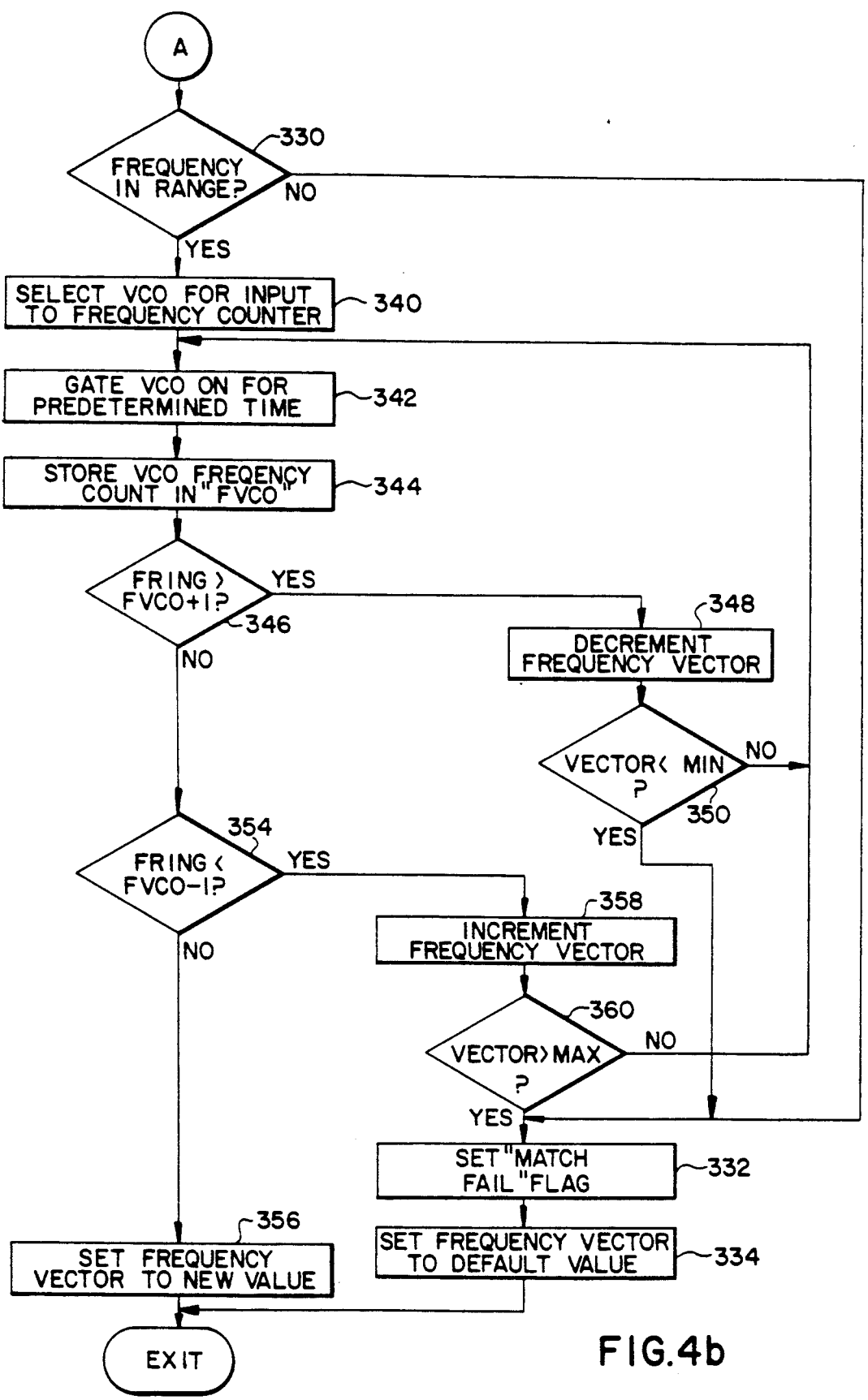

A flowchart of the frequency match routine is shown in FIGS. 4a and 4b. Referring to FIG. 4a, the routine begins execution at step 302 where several several parameters are initialized. These parameters include a "match fail" flag that is set to one upon failure of the frequency match routine. The frequency match routine is considered to fail in either of two cases: 1) when the average ringdown frequency of the transducer is not within an expected frequency range; and 2) when the frequency match routine is unable to adjust the frequency of the VCO 50 to match the average ringdown frequency.

Figure 5:
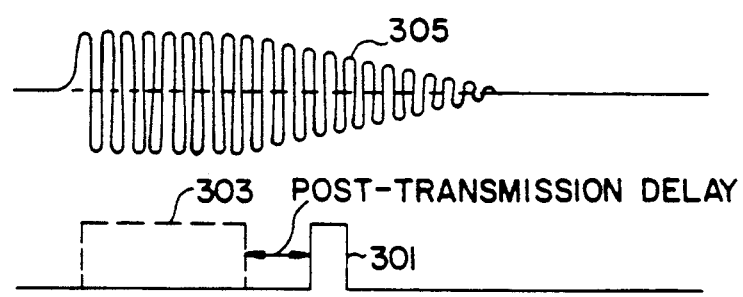
FIG. 5 is a diagram of several waveforms generated during the operation of the preferred embodiment.

Another parameter that is initialized during step 302 is a post-transmission delay period. Referring to FIG. 5, the ringdown frequency is measured with the use of a predetermined time interval 301, or "frequency gate." The frequency gate 301 opens after the post-transmission delay period, which is defined as the time period between the end of the transmission gate 303 and the beginning of the frequency gate 301. As described in more detail below, the frequency of the ringdown signal 305 is measured during the time interval defined by the frequency gate 301.

The ringdown frequency is measured by the frequency counter 150 in the following manner. The first zero-crossing occurring within the frequency gate starts the counter 150, and the second zero-crossing occurring within the gate stops the counter 150. The binary count so generated is directly proportional to the time between zero-crossings, and inversely proportional to the frequency of the ringdown signal. Thus, a larger count corresponds to a relatively lower frequency than a smaller count. Each of the counts of the counter 150 corresponds to about 50 Hz. The actual determination of the ringdown frequency during the frequency match routine is not necessary since all actions may be taken on the basis of the binary counts themselves.

Referring back to FIG. 4a, at step 304 a sampling index is set to 40 since 40 samples of the ringdown frequency are taken. The sampling index, which is decremented by one after each sample is taken, is used to determine when the sampling is completed.

At step 306, the current frequency vector is sent by the controller 40 to the 0/A converter 60. The frequency vector, which is a multi-bit digital signal, is converted by the converter 60 to an analog voltage that determines the frequency at which the VCO 50 oscillates. A new value of the frequency vector is determined each time the frequency match routine is executed. When the routine is first executed, the frequency vector is set to a predetermined value.

At step 308, the output of the zero-crossing detector 130 is selected for input to the frequency counter 150 by means of the select signal provided by the controller 40 on the line 144 to the multiplexer 140. At step 310, the gain of the amplifier 90 is set to its maximum value to ensure that the zero-crossing detector 130 generates a zero-crossing each time the echo signal falls below the zero axis.

Steps 312-322 are repeated each time a sample of the ringdown frequency is taken. At step 312 an energy burst is transmitted. At step 314, the frequency gate is opened after the completion of the post-transmission delay. At step 316, the count generated by the frequency counter 150 is added to an accumulator that stores the sum of the counts generated during all 40 samples. At step 318, a relatively small predetermined period of time is added to the post-transmission delay period in order to slightly shift the frequency gate. The purpose of shift the frequency gate is to ensure that a relatively broad portion of the ringdown signal is sampled. At step 320, the sampling index is decremented, and at step 322 the program branches back to step 312 if all the samples have not been taken.

At step 324 the average ringdown frequency count is determined by dividing the sum of the counts stored in the accumulator by the number of frequency samples that were taken. The average count is stored in a FRING variable.

Referring to FIG. 4b, at step 330 the program determines whether the average ringdown frequency is in its expected range by determining whether the average ringdown count is between a maximum count and a minimum count. If the ringdown frequency is not in the expected range, the program branches to step 332 where the "match fail" flag is set. The program then branches to step 334 where the frequency vector is set to an intermediate default value.

If the average ringdown frequency is in its expected range as determined at step 330, the program branches to step 340. The purpose of steps 340-356 is to set the VCO frequency, and thus the frequency at which ultrasonic energy bursts are transmitted by the transducer 16, to match the average ringdown frequency. At step 340, the VCO 50 is selected for input to the frequency counter 150 via the multiplexer select line 144.

At step 342, the VCO 50 is gated on for a predetermined period of time. When the VCO is gated on, the first pulse edge it generates starts the frequency counter 150 and the next pulse edge stops the counter 150. Thus, the binary count generated by the counter 150 relates to the VCO frequency the same way that the zero-crossings relate to the ringdown frequency as described above. At step 344 the VCO frequency count is stored in a FVCO variable.

Step 346 determines whether the average ringdown frequency count stored in FRING is greater than one more than the FVCO count. If it is, then the frequency of the VCO 50 needs to be lowered. Accordingly, the program branches to step 348 where the frequency vector is decremented. At step 350, the value of the frequency vector is compared to a minimum value. If the frequency vector is less than the minimum, the program branches to step 332 where the "match fail" flag is set. The program then proceeds to step 334 where the frequency vector is set to its intermediate default value.

If the decremented frequency vector was not less than the minimum value as determined at step 350, the program branches back to step 342 in order to measure the VCO frequency with the new value of the frequency vector.

If the average ringdown frequency count stored in FRING is not greater than one more than the FVCO count as determined at step 346, the program branches to step 354 where the FRING count is tested to determine whether it is less than one less than the FVCO count. If it is, then the frequency of the VCO needs to increased. Accordingly, the program branches to step 358 where the frequency vector is incremented.

At step 360, the value of the frequency vector is compared to a maximum value. If the frequency vector is greater than the maximum, the program branches to step 332 where the "match fail" flag is set. The program then proceeds to step 334 where the frequency vector is set to its intermediate default value.

If the FRING and FVCO counts were within one count of each other as determined at steps 346, 354, the program will branch to step 356 where the frequency vector is set to the new value. The frequency match routine then terminates.

Sonar Routine

The sonar routine is executed during each loop of the main operating routine. Thus, it is executed much more frequently than the frequency match routine described above.

During operation, the sonar routine transmits a predetermined number of energy bursts towards the liquid surface and determines the average round-trip travel time of those energy bursts. Any of the received echoes whose frequency is not substantially the same as the transmission frequency are disregarded in determining the average travel time.

Figure 6A:
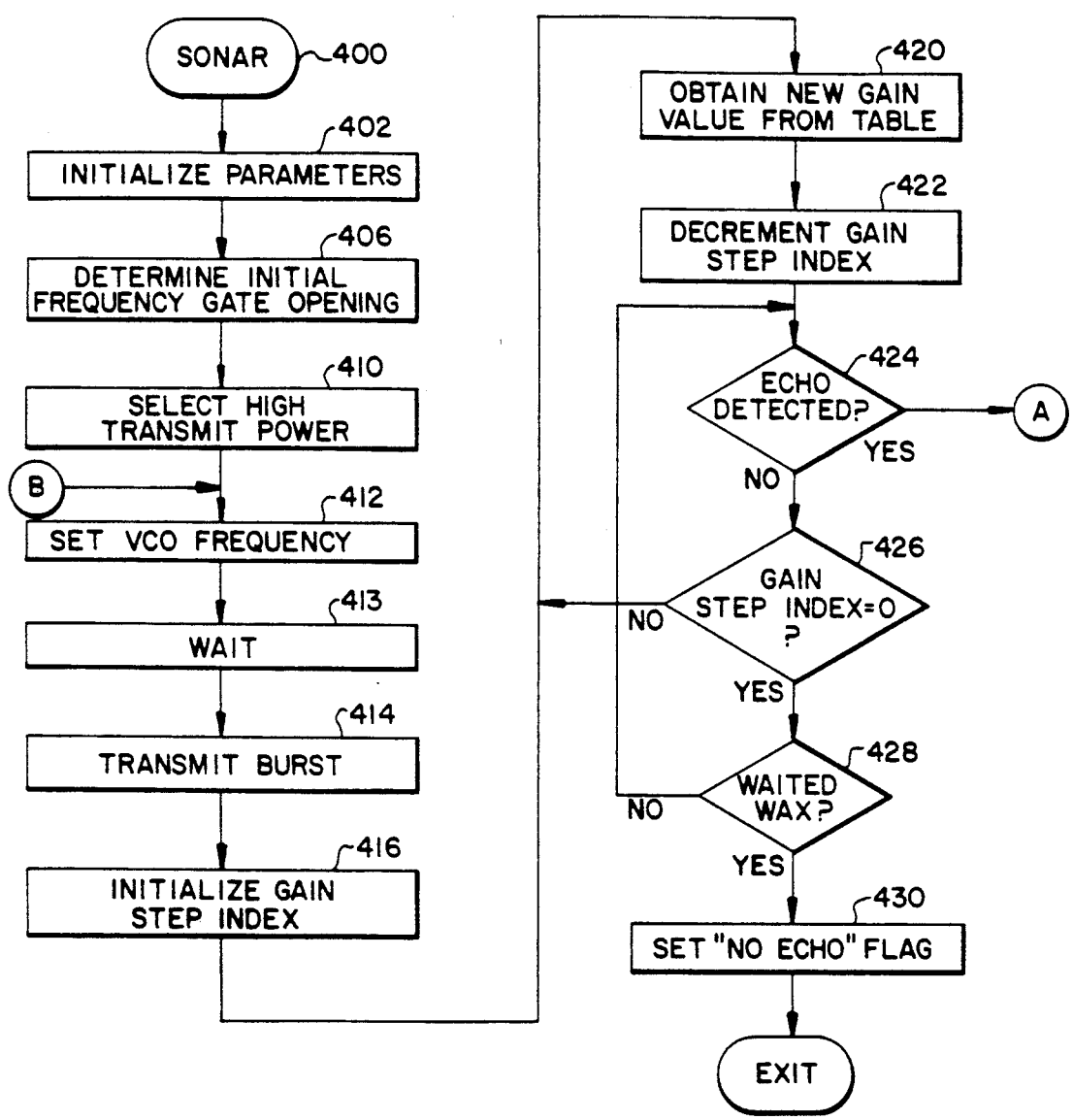
FIGS. 6a and 6b are a flowchart of the sonar routine schematically shown in the main operating routine of FIG. 3.
Figure 6B:
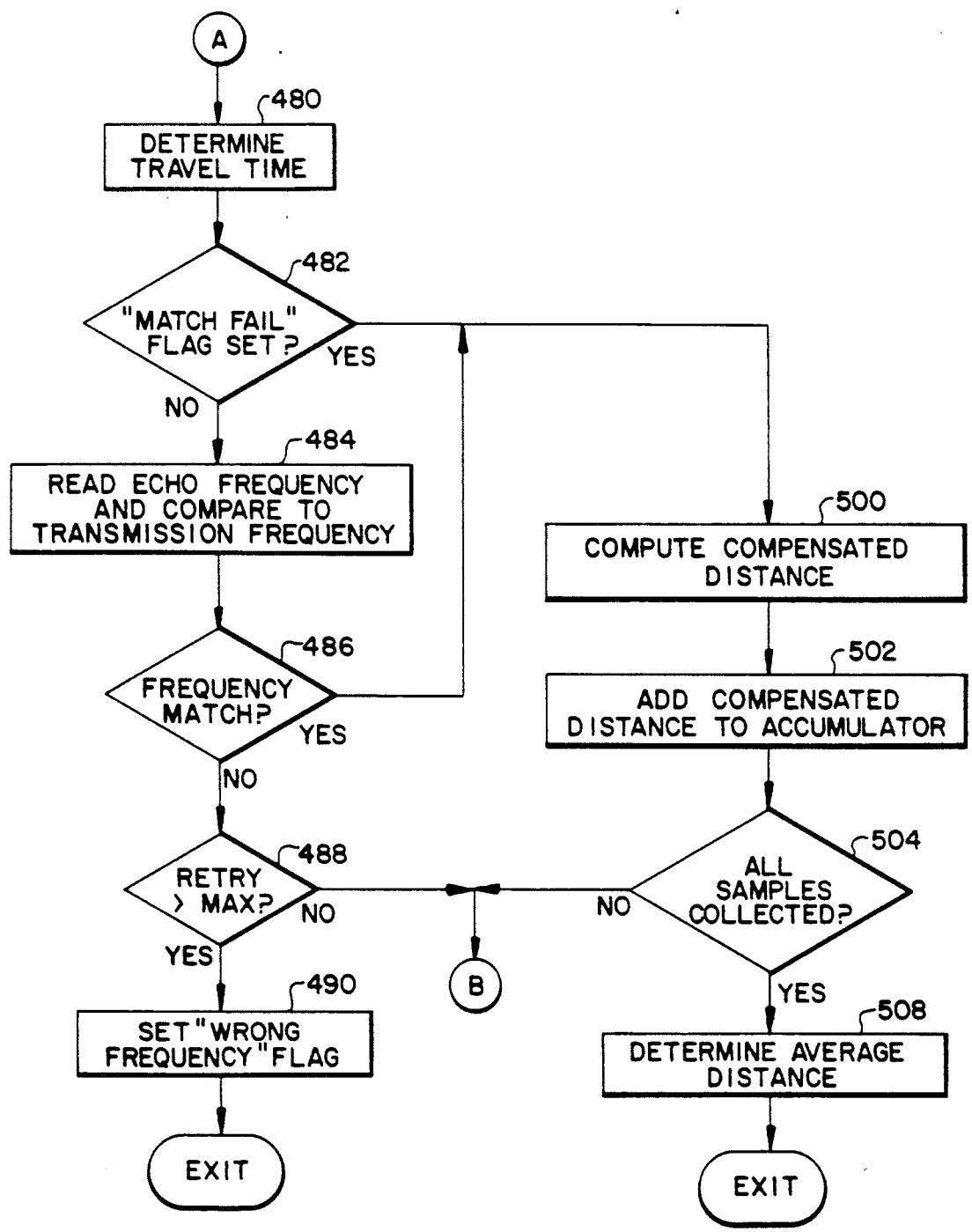

A flowchart of the sonar routine is shown in FIGS. 6a and 6b. Referring to FIG. 6a, the sonar routine begins operation at step 402 where a number of parameters are initialized. These parameters include a "no echo" flag which indicates that no echo was received during the sonar routine and a "wrong frequency" flag that indicates that none of the echoes received during the sonar routine had a frequency that matched the transmission frequency.

Figure 7:
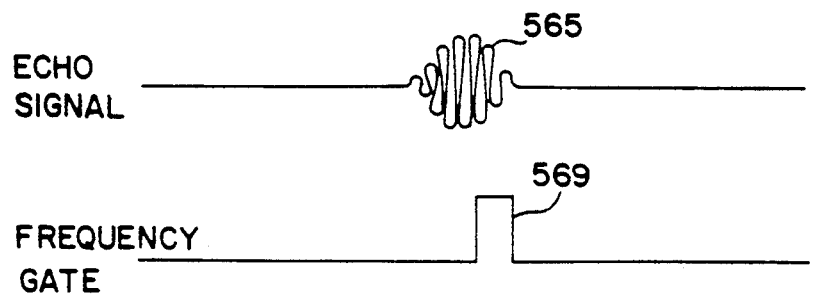
FIG. 7 is a diagram of an echo signal and a frequency gate generated during the operation of the preferred embodiment.

At step 406, the initial opening of the frequency gate is determined. The frequency gate in this case is shown in FIG. 7 as waveform 569. The frequency gate 569 is opened during the latter portion of the echo signal, which is shown in FIG. 7 as waveform 565. At step 410, the high power setting of the pulse generator 42 is selected by the controller 40 via the line 44.

At step 412, the frequency at which bursts are transmitted is specified by transmitting the current frequency vector to the VCO 50 via the D/A converter 60. At step 413, the program waits for old echoes to die out. This waiting period may be a predetermined period of time, or a time period that varies slightly within predetermined limits. At step 414 an energy burst is transmitted.

The gain of the detector 10 is gradually increased in an exponential fashion following the transmission of each burst during the sonar routine. This gradual increase in the gain compensates for the attenuation of energy bursts as they travel through the atmosphere within the tank 12. The gradual increase in the gain is achieved by a gain table stored in a read-only memory (not shown) in the controller 44. The gain table has a predetermined number of discrete gain settings having exponentially increasing values.

Steps 416–426 relate to the control of the gain after each energy burst is transmitted. At step 416, the gain step index is initialized to correspond to the number of discrete gain values in the gain table. At step 420, a new gain value is obtained from the gain table, based upon the current value of the gain step index, and used to control the gain of the amplifier 90. At step 422, the gain step index is decremented, and the program proceeds to step 424.

At step 424, if an echo has not yet been detected, as indicated by the first falling edge 138 of the output of the zero-crossing detector 130, the program branches to step 426 where the gain step index is tested to determine whether it is zero. If it is not zero, meaning that there are more gain values in the gain table, the program branches back to step 420 where the next gain value is obtained from the gain table and used to control the amplifier 90.

If the gain step index is zero, indicating that there are no more gain values left, the program branches to step 428, where it determines whether the program has waited the maximum amount of time for an echo to be received. This amount of time could correspond to the maximum range of the detector 10, which may be determined by the user.

If the maximum amount of time has elapsed, the program branches to step 430, where the "no echo" flag is set in the sonar status register to indicate that no echo was received. The sonar routine then terminates. If the maximum amount of time has not elapsed, the program branches back to step 424.

If an echo is detected as determined at step 424, the program branches to step 480 shown in FIG. 6b, where the round-trip travel time of the echo is determined. The travel time is determined as the difference between the falling edge of the transmit gate 303 (see FIG. 5) and the time at which the zero-crossing detector 130 generated the falling edge 138 in its output.

At step 482, the program determines whether the "match fail" flag is set. If the "match fail" flag is not set, indicating that the previous execution of the frequency match routine was successful, the program branches to step 484, where the frequency of the echo signal is compared to the burst transmission frequency. If the frequencies match, the program branches to step 500. If the "match fail" flag is set as determined at step 482, the frequency of the echo is not checked, and the program branches to step 500.

If there is a frequency mismatch at step 486, the program branches to step 488, where the number of retry attempts made thus far is compared to a maximum. If no more retries are to be made, the program branches to step 490 where the "wrong frequency" flag is set. The sonar routine then terminates.

If another retry is to be made, the program branches from step 488 back to step 412 to transmit another energy burst.

At step 500, the compensated distance to the liquid level is computed based upon the travel time determined in step 480 and either the most recent temperature reading or travel time to the reference reflector. At step 502, the compensated distance is added to an accumulator, and at step 504 the program determines whether all the samples have been collected. If all the samples have not been collected, the program branches back to step 412 for the transmission of another burst.

If all the samples have been collected, the program branches to step 508 where the average compensated distance to the liquid surface is computed by dividing the distance sum stored in the accumulator of step 502 by the number of samples that were taken.

Many modifications and alternative embodiments of the invention will be apparent to those of ordinary skill in the art in view of the foregoing description of the preferred embodiment. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A detector, comprising:
   a transducer for generating a burst of energy at a transmission frequency, said transducer generating a ringdown signal at a ringdown frequency;
   means coupled to said transducer for detecting the ringdown frequency of said transducer; and
   means coupled to said transducer for automatically adjusting said transmission frequency so that it substantially matches said ringdown frequency.

2. A detector as defined in claim 1 wherein said means for automatically adjusting said transmission frequency adjusts said transmission frequency to within a predetermined frequency range of said ringdown frequency.

3. A detector as defined in claim 2 wherein said predetermined frequency range includes only those frequencies which differ from said ringdown frequency by about one percent.

4. A detector as defined in claim 1 wherein said means for detecting the ringdown frequency of said transducer comprises:
   a zero-crossing detector that generates a pair of zero-crossings from said ringdown signal; and
   a counter that generates a binary count related to the time between said pair of zero-crossings.

5. A detector as defined in claim 1 wherein said means for adjusting said transmission frequency comprises a voltage-controlled oscillator.

6. A detector as defined in claim 5 wherein said means for adjusting said transmission frequency additionally comprises a controller.

7. A detector as defined in claim 1 wherein said ringdown signal is generated via an excitation signal provided to said transducer and wherein said means for detecting the ringdown frequency of said transducer comprises means for detecting the frequency of said ringdown signal during a time interval between the end of said excitation signal and the receipt of an echo of said ringdown signal by said transducer.

8. A detector, comprising:

a transducer that generates bursts of energy at a transmission frequency, said transducer generating ringdown signals at a ringdown frequency;

means coupled to said transducer for detecting the ringdown frequency of said transducer;

means coupled to said ringdown frequency detecting means for determining the average ringdown frequency corresponding to a number of said ringdown signals; and means coupled to said transducer for adjusting said transmission frequency based upon said average ringdown frequency.

9. A detector as defined in claim 8 wherein said ringdown signals are generated via excitation signals provided to said transducer and wherein said means for detecting the ringdown frequency of said transducer comprises means for detecting the frequency of said ringdown signals during time intervals between the end of said excitation signals and the receipt of echoes of said ringdown signals by said transducer.

10. A detector, comprising:

a transducer that generates bursts of energy at a transmission frequency, said transducer generating ringdown signals at a ringdown frequency;

detecting means coupled to said transducer for detecting the ringdown frequency of said transducer;

gate generation means for generating a frequency gate signal that determines when said detecting means detects said ringdown frequency, said detecting means being responsive to said ringdown signal during the period of time determined by said frequency gate, said gate generation means shifting said frequency gate so that a different portion of said ringdown signal is detected by said detecting means; and means coupled to said transducer for automatically adjusting said transmission frequency based upon said ringdown frequency.

11. A detector, comprising:

a transducer for generating a burst of energy at a transmission frequency, said transducer generating a ringdown signal at a ringdown frequency;

means coupled to said transducer for detecting the ringdown frequency of said transducer; and means coupled to said transducer for automatically adjusting said transmission frequency based upon said ringdown frequency.

12. A detector as defined in claim 11 wherein said ringdown signal is generated via an excitation signal provided to said transducer and wherein said means for detecting the ringdown frequency of said transducer comprises means for detecting the frequency of said ringdown signal during a time interval between the end of said excitation signal and the receipt of an echo of said ringdown signal by said transducer.

13. A method of automatically adjusting the frequency at which a detector generates energy bursts, said method comprising the steps of:

(a) transmitting a burst of energy at a transmission frequency and generating a ringdown signal associated with the transmission of said burst of energy;

(b) detecting the frequency of said ringdown signal; and (c) automatically adjusting the frequency at which a burst of energy is transmitted based upon the frequency of said ringdown signal detected in said step (b).

14. A method as defined in claim 13 wherein said ringdown signal is generated via the step of providing an excitation signal to said transducer and wherein said step (b) is performed during the time interval between the end of said excitation signal and the receipt of an echo of said ringdown signal by said transducer.

15. A method as defined in claim 13 wherein the frequency of said ringdown signal is detected in said step (b) by determining the time difference between successive zero-crossings of the ringdown signal.

16. A method as defined in claim 13 wherein said steps (a), (b) and (c) are periodically repeated during operation of the detector.

17. A method of automatically adjusting the frequency at which a detector generates energy bursts, said method comprising the steps of:

(a) transmitting a burst of energy at a transmission frequency and generating a ringdown signal associated with the transmission of said burst of energy;

(b) detecting the frequency of said ringdown signal;

(c) repeating said steps (a) and (b) to generate a signal relating to the average frequency of said ringdown signal; and (d) automatically adjusting the frequency at which a burst of energy is transmitted based upon the signal relating to the average frequency of said ringdown signal generated in said step (c).

18. A method as defined in claim 17 wherein said signal generated in said step (c) comprises an average binary count that is inversely proportional to the average ringdown frequency.

19. A method as defined in claim 17 wherein said ringdown signal is generated via the step of providing an excitation signal to said transducer and wherein said step (b) is performed during the time interval between the end of said excitation signal and the receipt of an echo of said ringdown signal by said transducer.

20. A method of automatically adjusting the frequency at which a detector generates energy bursts, said method comprising the steps of:

(a) transmitting a first burst of energy at a transmission frequency and generating a ringdown signal associated with the transmission of said first burst of energy;

(b) generating a frequency gate during a first portion of the ringdown signal generated in said step (a);

(c) detecting the frequency of said ringdown signal at a time within said frequency gate generated during said step (b);

(d) transmitting a second burst of energy at a transmission frequency and generating a ringdown signal associated with the transmission of said second burst of energy;

(e) generating a frequency gate during a second portion of the ringdown signal generated in said step (d), said frequency gate of said step (e) being shifted with respect to the frequency gate of said step (b);

(f) detecting the frequency of said ringdown signal at a time within said frequency gate generated during said step (e); and (g) automatically adjusting the frequency at which a burst of energy is transmitted based upon the frequency of said ringdown signals as detected in said steps (b) and (e).

* * * * *

UNITED STATES PATENT AND TRADEMARK OFFICE
CERTIFICATE OF CORRECTION

PATENT NO. : 5,277,065

DATED : January 11, 1994

INVENTOR(S) : Nicholas Leszczynski

It is certified that error appears in the above-identified patent and that said Letters Patent is hereby corrected as shown below:

Column 9, line 30, please delete "shift" and substitute --shifting-- therefore.

Signed and Sealed this

Second Day of August, 1994

Attest:

BRUCE LEHMAN

*Attesting Officer*     *Commissioner of Patents and Trademarks*